US009878081B2

United States Patent
Leiendecker et al.

(10) Patent No.: US 9,878,081 B2
(45) Date of Patent: Jan. 30, 2018

(54) ARRANGEMENT COMPRISING MEDICAL TREATMENT UNITS AND PERIPHERAL DEVICES AS WELL AS A PERIPHERAL DEVICE AND TREATMENT UNIT FOR USE IN SUCH AN ARRANGEMENT

(75) Inventors: Claus Leiendecker, Schweinfurt (DE); Carsten Müller, Euerbach (DE); Elke Schulte, Schweinfurt (DE); Wei Zhang, Niederwerrn (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 853 days.

(21) Appl. No.: 12/596,613

(22) PCT Filed: Apr. 17, 2008

(86) PCT No.: PCT/EP2008/003060
§ 371 (c)(1),
(2), (4) Date: Oct. 19, 2009

(87) PCT Pub. No.: WO2008/128696
PCT Pub. Date: Oct. 30, 2008

(65) Prior Publication Data
US 2010/0114639 A1    May 6, 2010

(30) Foreign Application Priority Data
Apr. 20, 2007   (DE) .................. 10 2007 018 741

(51) Int. Cl.
*G06Q 50/22*     (2012.01)
*A61M 1/14*      (2006.01)
(Continued)

(52) U.S. Cl.
CPC .............. *A61M 1/14* (2013.01); *A61B 90/90* (2016.02); *A61B 90/98* (2016.02); *G06Q 50/24* (2013.01);
(Continued)

(58) Field of Classification Search
CPC .... G06Q 50/22; G06F 19/3418; A61B 5/0002
(Continued)

(56) References Cited

U.S. PATENT DOCUMENTS 5,827,180 A   10/1998   Goodman
6,332,094 B1 *   12/2001   Gorman ................ A61B 5/222
600/520

(Continued)

FOREIGN PATENT DOCUMENTS

DE   102005059131   12/2005
EP   1 574 164   9/2005
(Continued)

OTHER PUBLICATIONS

PCT International Search Report and Written Opinion for PCT/EP08/003060, dated Dec. 29, 2008.
(Continued)

*Primary Examiner* — Joy Chng
(74) *Attorney, Agent, or Firm* — Kilyk & Bowersox, P.L.L.C.

(57) ABSTRACT

An assembly includes at least two medical treatment units, each of which can be allocated to a patient and at least two peripheral devices, each of which can be allocated to a patient. The peripheral devices and the treatment units have means for allocating a peripheral device to a treatment unit and means for verifying the allocation of a peripheral device to a patient. To allocate a peripheral device to a treatment unit, the peripheral device is placed by operators in a receiving unit belonging to the treatment unit. Said receiving unit is preferably designed as a charging station for the battery of the peripheral device. In the event of a successful allocation of peripheral device and patient, confirmed by the receipt of physiological data of the patient, the operators verify the correct allocation of a peripheral device to the
(Continued)

patient and must confirm the correct allocation by confirmation means. The peripheral device is only released if the operator has confirmed the correct allocation, preferably within a predefined time period.

18 Claims, 4 Drawing Sheets

(51) Int. Cl.
    *G06Q 50/24*     (2012.01)
    *A61B 90/90*     (2016.01)
    *A61B 90/98*     (2016.01)
    *A61B 5/021*     (2006.01)
    *A61B 5/024*     (2006.01)
    *A61B 17/00*     (2006.01)
    *A61B 5/00*     (2006.01)

(52) U.S. Cl.
    CPC ............... *A61B 5/002* (2013.01); *A61B 5/021* (2013.01); *A61B 5/024* (2013.01); *A61B 2017/00119* (2013.01); *A61B 2017/00221* (2013.01); *A61B 2017/00482* (2013.01); *A61B 2562/08* (2013.01); *A61M 2205/3569* (2013.01); *A61M 2205/3576* (2013.01); *A61M 2205/6018* (2013.01); *A61M 2205/6054* (2013.01); *A61M 2205/8237* (2013.01); *A61M 2205/84* (2013.01)

(58) Field of Classification Search
    USPC ........................................................ 705/2–3
    See application file for complete search history.

(56) References Cited

U.S. PATENT DOCUMENTS

| | | | | |
|---|---|---|---|---|
| 2001/0034614 | A1* | 10/2001 | Fletcher-Haynes | A61M 1/3496 705/2 |
| 2004/0019464 | A1* | 1/2004 | Martucci | G06F 19/3412 702/189 |
| 2005/0027563 | A1* | 2/2005 | Fackler | G06Q 10/10 705/2 |
| 2005/0055244 | A1* | 3/2005 | Mullan | G06Q 50/22 705/2 |
| 2005/0180615 | A1* | 8/2005 | Gerder | A61B 5/117 382/124 |
| 2006/0025663 | A1* | 2/2006 | Talbot | A61B 5/0002 600/365 |
| 2008/0097231 | A1* | 4/2008 | Balda | A61B 5/02438 600/509 |
| 2008/0312960 | A1 | 12/2008 | Nikolic et al. | |
| 2009/0184842 | A1* | 7/2009 | Baldus | G06F 19/323 340/870.07 |

FOREIGN PATENT DOCUMENTS

| | | |
|---|---|---|
| JP | 02-068070 | 3/1990 |
| WO | WO 2004/056263 | 7/2004 |

OTHER PUBLICATIONS

International Preliminary Report on Patentability for PCT/EP2008/03060, dated Nov. 10, 2009.

* cited by examiner

ARRANGEMENT COMPRISING MEDICAL TREATMENT UNITS AND PERIPHERAL DEVICES AS WELL AS A PERIPHERAL DEVICE AND TREATMENT UNIT FOR USE IN SUCH AN ARRANGEMENT

FIELD OF THE INVENTION

The present invention relates to an arrangement comprising at least two medical treatment units and at least two peripheral devices, wherein one medical treatment unit of the at least two medical treatment units and one peripheral device of the at least two peripheral devices is to be allocated to a patient and the peripheral device to be allocated to the patient is to be allocated to the medical treatment unit to be allocated to the patient. Moreover, the present invention relates to a peripheral device and a treatment unit for use in such an arrangement.

BACKGROUND

In medical technology, various treatment units, to which patients are connected or which are connected to patients, are used for the treatment of patients. The connection between patient and machine generally takes place via tubes and/or lines. The known treatment units include, for example, dialysis machines with an extracorporeal blood circuit.

It is known to operate medical treatment units together with one or more peripheral devices. Such satellites serve, for example, to monitor the patient during the treatment, the ascertained patient-specific data being transmitted to the treatment unit.

During dialysis, for example, physiological data of the dialysis patient are detected with various sensors. An attempt is made to ensure that the connection between patient and dialysis machine and the peripheral device consists only of the necessary blood tubes of the extracorporeal blood circuit and as few other lines as possible.

Whereas a fixed connection exists between the treatment unit and the patient via the tubes, the data transmission between the peripheral device and the treatment unit can take place wirelessly, for example by radio or light signals. Consequently, the operative can immediately detect the allocation between the treatment unit and the patient on the basis of the fixed connection, but not the allocation between the peripheral device and the treatment unit.

If a plurality of treatment units and peripheral devices are operated together in a treatment area, it is necessary to allocate in each case one treatment unit and one peripheral device to a patient and to produce a connection from the respective peripheral device to the respective treatment unit.

An incorrect allocation between the peripheral device and the treatment unit on the one hand and the peripheral device and the patient on the other hand can in the extreme case lead to life-threatening complications during the treatment. This is especially problematic when the incorrect allocation is not detected immediately on account of a cableless connection.

If a plurality of devices which are communicating with one another are operated at the same time, use is generally made of so-called identification (ID) signals, with which it can be detected whether the signals of the one or the other satellite are being received. U.S. Pat. No. 6,332,094 B1, for example, describes a pulsometer, which transmits pulse signals together with an identification signal wirelessly to a receiver.

International Application Publication No. WO 20041056263 A1 describes a method for the wireless transmission of signals between a plurality of peripheral devices and a plurality of treatment units. Allocated to the treatment units is a plurality of receivers, which receive the signals of the peripheral devices. The readiness of the receiver for receiving the signals of the peripheral devices is produced by the fact that the peripheral device notifies the receiver. Only in the state of readiness for reception does the receiver convert the signals of the peripheral device which are transmitted to the respective treatment unit.

There is known from U.S. Pat. No. 6,870,475 B2 a charging station for charging the battery of a portable medical monitoring unit, which serves for the monitoring of patient-specific data. The patient monitoring system provides a large number of charging stations at different points, into which the patient can insert the monitoring unit in order to charge the battery. Patient-specific data of the portable monitoring units can be transmitted wirelessly to a central monitoring unit.

U.S. Pat. No. 6,184,651 B1 and U.S. Pat. No. 5,455,466 describe in general terms charging stations for charging the battery of electrical devices, wherein an inductive coupling takes place between the electrical device and the charging station.

The problem underlying the invention is to increase the reliability and flexibility during the operation of at least two medical treatment units and peripheral devices.

SUMMARY

The reliability and flexibility during the operation of a plurality of medical treatment units and peripheral devices is increased with the arrangement according to example embodiments of the invention by the fact that the operative acknowledges, after allocation of a treatment unit to a patient and a peripheral device to a patient, that the patient to whom the peripheral device has been allocated is the patient to whom the treatment unit, to which the peripheral device has been allocated, has been allocated. The peripheral device is released only on condition that the correct allocation of peripheral device and patient has been acknowledged. This thus eliminates the situation where, although the correct peripheral device is allocated to the correct treatment unit, the peripheral device allocated to the treatment unit is allocated to the wrong patient.

The means for releasing the peripheral device can be designed in such a way that the patient-specific data is not transmitted to the treatment unit or received or evaluated by the treatment unit until the correct allocation of the peripheral device and patient has been acknowledged. The means for releasing the peripheral device can for example also be designed in such way that the medical treatment cannot be started until the correct allocation of the peripheral device and patient has been acknowledged.

In a preferred embodiment of the invention, the means for allocating a peripheral device to a treatment unit comprises means for sending an address for identification of the peripheral device to the medical treatment unit and means for receiving the address for identification of the peripheral device by the treatment unit. For example, the address can be an MAC address (media access control), which is used for the unequivocal identification of the peripheral device in the network.

A further preferred embodiment makes provision such that the means for allocating the peripheral device and the treatment unit comprises means for accommodating a peripheral device and means for detecting a peripheral device accommodated in the means for accommodating a peripheral device. The means for accommodating a peripheral device can be unequivocally allocated to a treatment unit, this allocation being able to be immediately detected by the operative. For example, the means for accommodating a peripheral device is arranged in close proximity to the treatment unit or is a component of the treatment unit. The peripheral device is unequivocally allocated to the treatment unit when the peripheral device is located in the means allocated to the treatment unit for accommodating a peripheral device.

The means for accommodating a peripheral device can be designed in different ways. For example, the means for accommodating a peripheral device can be an accommodation unit into which the peripheral device is placed. The peripheral device can be placed loosely into the accommodation unit or also be secured in the accommodation unit.

The means for detecting the peripheral device in the accommodation unit can also be designed differently. For example, the means for detecting the peripheral device can comprise mechanical contact makers, with which it can be detected whether the peripheral device is located in the accommodation unit. Alternatively, the means for detecting the peripheral device can comprise optical or inductive sensors.

A particularly advantageous embodiment, which offers great advantages in practice, makes provision such that the means for accommodating a peripheral device comprises means for charging a battery for the power supply of the peripheral device. The accommodation units can be designed as charging stations for the peripheral devices. The accommodation units thus ensure not only the allocation of the peripheral device and the treatment unit, but also the permanent operation of the peripheral devices.

In a further particularly preferred embodiment, the peripheral device sends the address for identification to the treatment unit when the peripheral device has been detected in the accommodation unit. The identification of the peripheral device therefore takes place fully automatically upon insertion of the peripheral device into the accommodation unit. It is however also possible for the peripheral device to send the identification address continuously and for the treatment unit to evaluate the identification address only after detection of the peripheral device in the accommodation unit.

The successful allocation of the peripheral device and the patient is preferably signaled by the peripheral device to the treatment unit by the fact that the peripheral device sends a corresponding signal to the treatment unit. For this purpose, the means for checking the allocation of the peripheral device and patient preferably comprise means for sending and receiving signals, in particular means for the wireless transmission of signals, for example a radio transmitter and a radio receiver. Other wireless transmission links, for example an optical data transmission, are however also possible.

It is concluded that there is a successful allocation of the peripheral device and patient preferably when the peripheral device receives patient-specific data for the monitoring of the patient, which presupposes that the peripheral device is connected to the patient. It is, however, also possible to provide additional sensors which detect the position of the peripheral device, for example contact makers on the tubes and/or lines.

The reliability can, furthermore, be increased by the fact that the operative is prompted, within a preset time interval, to allocate to the patient the peripheral device which is allocated to the treatment unit and removed from the accommodation unit. A particularly preferred embodiment makes provision such that the means for checking the allocation of the peripheral device and patient cooperate with means for measuring the time after removal of the peripheral device from the means for accommodating the peripheral device. The means for checking the allocation of the peripheral device and patient preferably cooperate with means for displaying the remaining time in the preset time interval, in order to signal to the operative how much time still remains in order to connect the peripheral device to the patient.

If the peripheral device is allocated to the patient only after the lapse of the preset time interval, the successful allocation of the peripheral device and patient is not signaled to the treatment unit. The operative is therefore forced to place the peripheral device back into the accommodation unit, in order to be able to carry out again the allocation of the peripheral device, treatment unit and patient within the preset time interval. This prevents the peripheral device, removed from the accommodation unit, being carried around by the operative for an indeterminate time, because in this case there is a particularly great risk of an incorrect allocation of the peripheral device and patient.

The prompting after the lapse of the preset time interval to insert the peripheral device back into the accommodation unit preferably takes place with means for emitting an optical and/or acoustic signal, which the means for checking the allocation for the peripheral device and patient preferably comprise.

The means for acknowledging the allocation of the treatment unit, peripheral device and patient preferably comprise means for manual input, for example switches, pushbuttons etc. The means for the manual input can also be designed as sensors which operate in a contactless manner, for example inductive switches etc.

The invention is based on the fact that the allocation of the treatment unit and patient requires a fixed connection of patient and treatment unit, so that this allocation is unequivocal for the operative. In the case where the medical treatment unit is, for example, a blood treatment apparatus, the fixed allocation of the treatment unit and patient is provided by the blood tube system, so that mistakes are ruled out in practice.

The peripheral devices may be designed differently and have different functions. For example, the peripheral devices may comprise one or more sensors for detecting patient-specific data, for example for measuring physiological measured values, such as blood pressure or pulse etc.

An example embodiment of the invention is explained below in greater detail by reference to the drawings.

DETAILED DESCRIPTION

Figure 1:
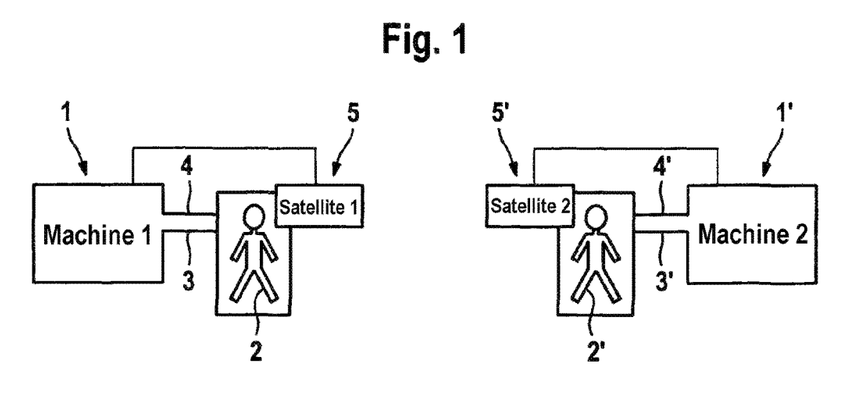
FIG. 1 shows a schematic representation of a correct allocation between two peripheral devices and treatment units to the respective patient.

FIG. 1 shows two medical treatment units 1, 1', for example, extracorporeal blood treatment apparatuses with an extracorporeal blood circuit. A patient 2, 2' is connected to each treatment unit 1, 1'. In the case of an extracorporeal blood treatment, patient 2, 2' is connected to blood treatment apparatus 1, 1' via a venous and arterial tube line 3, 4; 3', 4'. A fixed allocation between the patient and the treatment unit is thus made. Moreover, a peripheral unit or device 5, 5', for example a blood pressure monitor, is allocated in each case to the two patients 2, 2'.

Peripheral devices 5, 5' monitor the patient's bodily function, for example the blood pressure or pulse, and transmit the physiological data to the respective treatment unit, to which the patient is connected.

Figure 2:
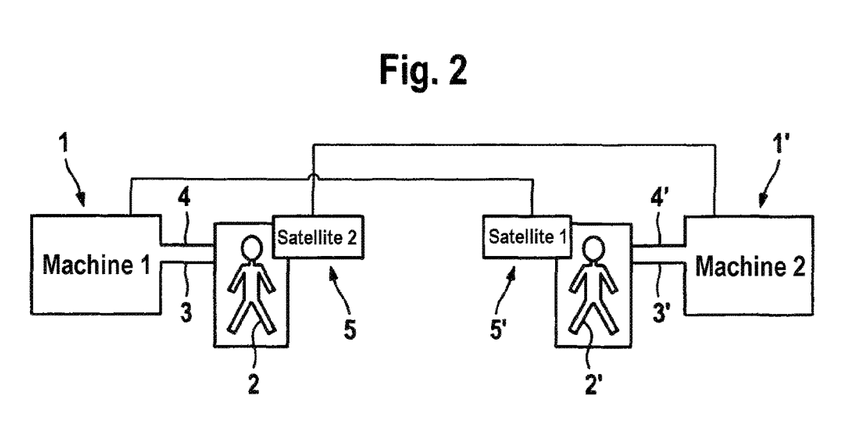
FIG. 2 shows the arrangement of FIG. 1, wherein the peripheral devices allocated to the respective treatment unit have been allocated to the wrong patient.

FIG. 1 shows the correct allocation of the peripheral device and patient on the one hand and the peripheral device and treatment unit on the other hand, while FIG. 2 shows an incorrect allocation of the peripheral device and patient and, respectively, the peripheral device and treatment unit. In the case of an incorrect allocation, treatment unit 1 receives the data of peripheral device 5' of patient 2', who is not connected to treatment unit 1, but rather to treatment unit 1'.

The arrangement according to example embodiments of the invention comprises at least two medical treatment units and peripheral devices. The individual components of a treatment unit and a peripheral device as well as the individual steps for the allocation of the treatment unit, the peripheral device and the patient are described below by reference to FIGS. 3, 4A, and 4B.

Figure 3:
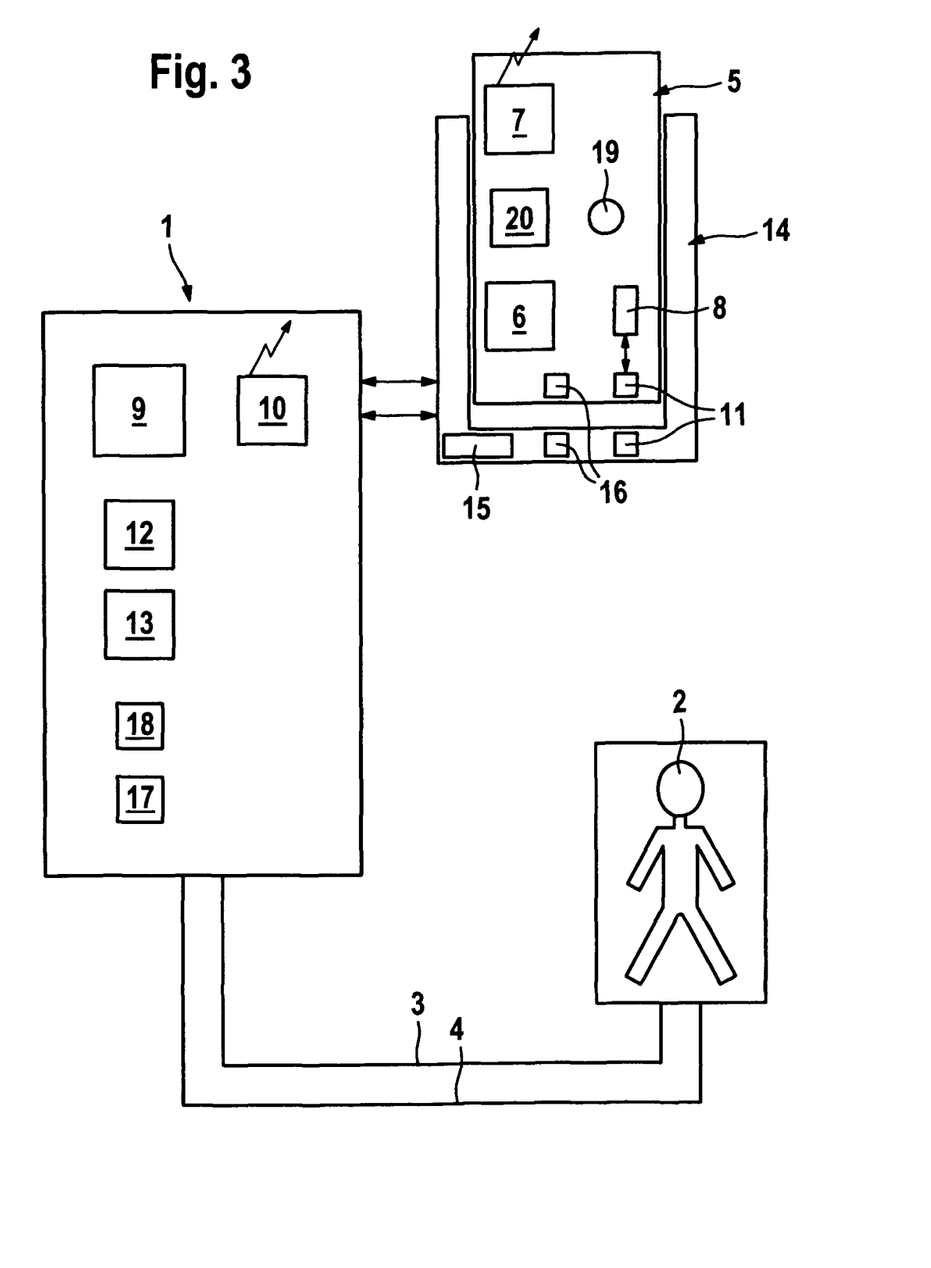
FIG. 3 shows the main components of a medical treatment unit and a peripheral device in a schematic representation.

Peripheral device 5, for example a blood pressure monitor, has various sensors 6 shown solely schematically for monitoring the patient, for example sensors for measuring the blood pressure or pulse. For bi-directional communication with respective treatment unit 1, peripheral device 5 has means 7 for sending and receiving signals, in particular a radio transmitter/receiver 7. The data transmission may, however, also take place solely directionally from the peripheral device to the treatment unit. Rechargeable battery 8 (accumulator) serves as the power supply of the peripheral device.

Furthermore, peripheral device 5 has means 19, with which the operative can acknowledge that the patient to whom the peripheral device has been allocated is the patient to whom the treatment unit has been allocated to which the peripheral device has been allocated. This means is preferably means for manual input, in particular a pushbutton 19.

Treatment unit 1, for example a blood treatment apparatus with an extracorporeal blood circuit, has various components 9, represented only schematically, for the treatment of patient 2, for example a dialyser, pumps etc. Patient 2 is fixedly connected to blood treatment apparatus 1, for example via a venous and arterial blood line 3,4. A fixed allocation between patient and treatment unit is thus produced.

For the communication with respective peripheral device 5, treatment unit 1 has means 10 for sending and receiving signals, in particular a radio transmitter/receiver 10 for a bi-directional data transmission. The data transmission between peripheral device 5 and treatment unit 1 thus takes place by radio, whereby the transmitter and receiver, as well as the interfaces required for this, are generally known to the person skilled in the art.

Treatment unit 1, moreover, has an optical and/or acoustic alarm emitter 12 and a display unit 13.

An accommodation unit 14 is fixedly allocated to each treatment unit 1, so that the operative can immediately detect that accommodation unit 14 belongs to blood treatment unit 1. Accommodation unit 14 is designed as a charging station. It comprises means 15 for the power supply, in particular a power pack, with which battery 8 of the peripheral device can be charged when the peripheral device is inserted into the accommodation unit. The electrical connection between power pack 15 and battery 8 can take place via suitable plug-in connections 11 or an inductive coupling.

Peripheral device 5 and/or accommodation unit 14 have means 16 for detecting whether peripheral device is inserted into the accommodation unit. This means may, for example, be electrical contact makers, which are provided either on the peripheral device or the accommodation unit or on both devices.

Figure 4A:
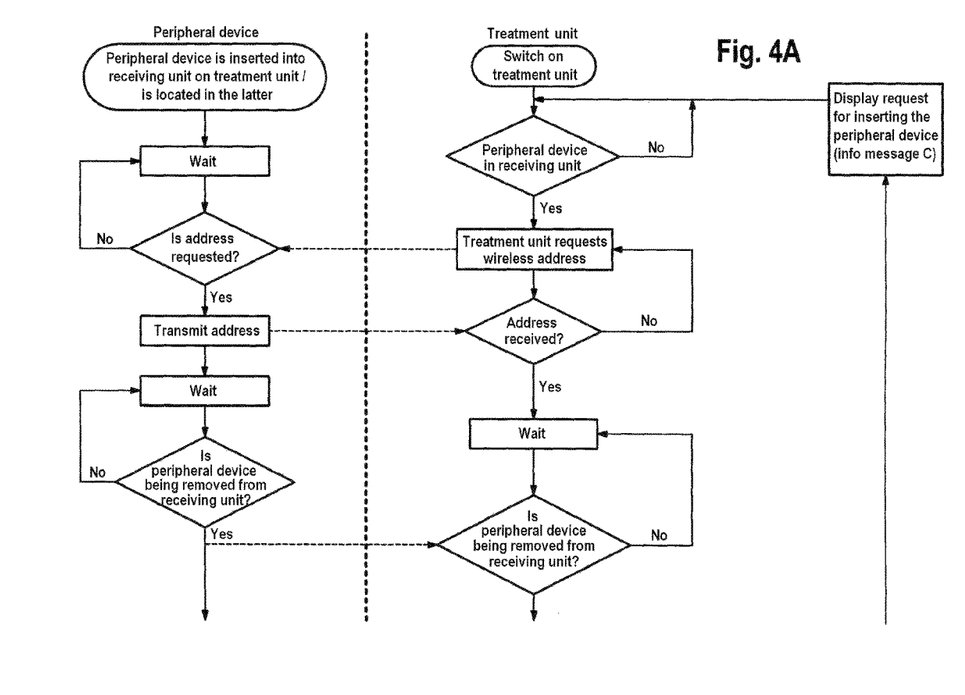
FIGS. 4A and 4B show a flow diagram, which describes the sequence of the allocation of the peripheral device and the treatment unit as well as the patient.
Figure 4B:
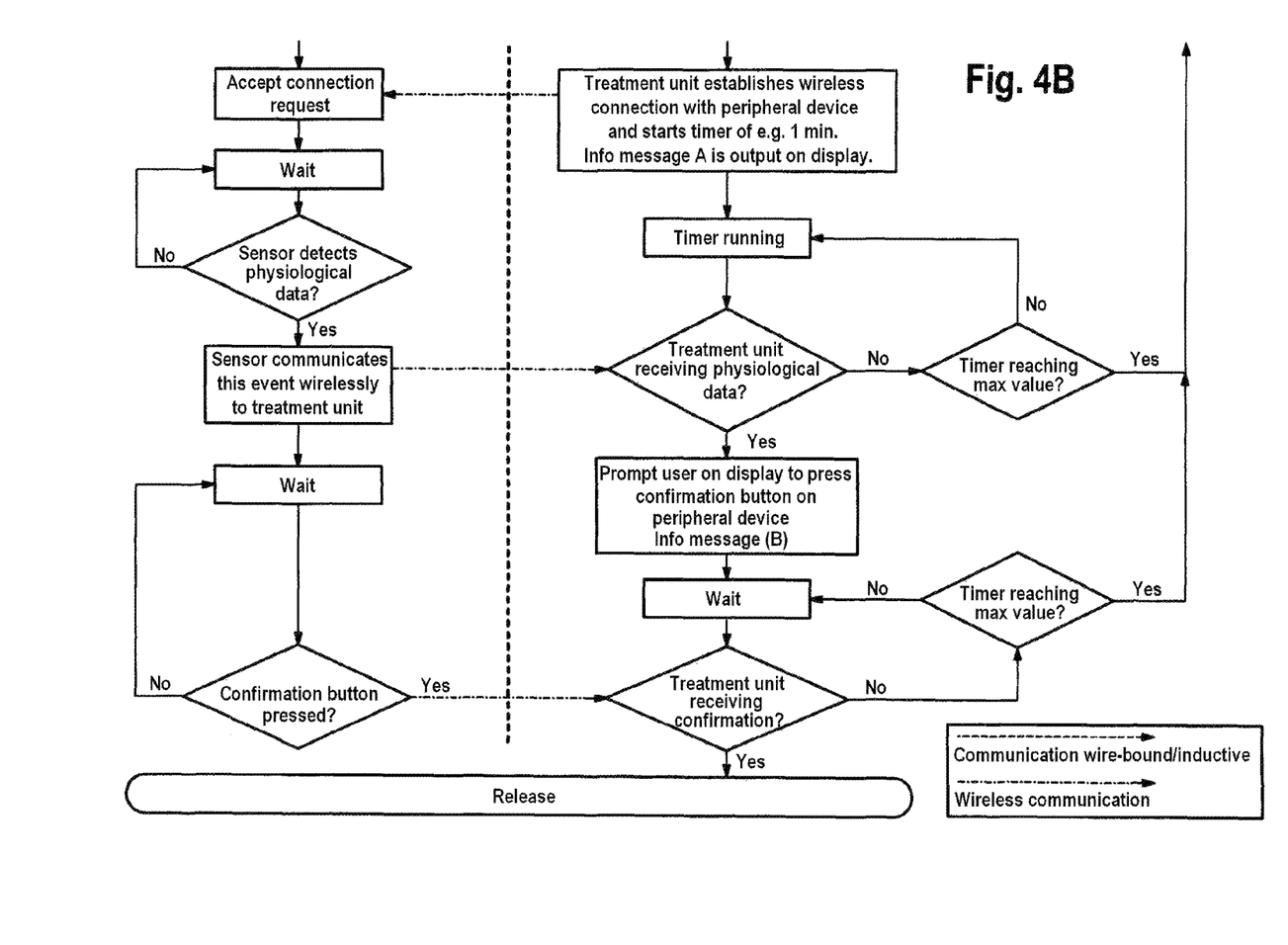

The function of the treatment units and peripheral devices is described in detail below by reference to FIGS. 3, 4A, and 4B.

It is assumed that the patients are connected to treatment units 1, for example extracorporeal blood treatment apparatuses, via venous and arterial blood lines 3, 4, so that in each case a fixed allocation of patient and treatment unit is produced, which can immediately be seen by the operative. The operative now has the task of connecting the peripheral device belonging to the treatment unit to the respective patients.

Respective peripheral device 5 is first inserted into accommodation unit 14, which is allocated to respective treatment unit 1. The operative has thus allocated the peripheral device to be treatment unit.

Means 16 detects that the peripheral device is located in accommodation unit 14. This is signalled by means 16 with a status signal. While peripheral device 5 is located in accommodation unit 14, an electrical connection is produced between power pack 15 and battery 8, so that the battery is charged.

Treatment unit 1 continuously inquires whether the status signal, indicating that the peripheral device is located in the accommodation unit, has been generated. If this is the case, radio transmitter/receiver 7 of peripheral device 5 sends an address for the identification of the peripheral device, for example an MAC address, to treatment unit 1, which receives the MAC address via radio transmitter/receiver 10. Treatment unit 1 has thus identified peripheral device 5.

For the identification of the peripheral devices by the exchange of MAC addresses, use is preferably made of transmission/reception means with a relatively short range in the case of a wireless transmission of the signals. If the range of the transmission/reception means is not greater than the distance between the peripheral device and the treatment unit with the respective accommodation unit, it can be ensured that the peripheral device communicates solely with its "own charging shell". For this purpose, the transmission means can also limit the range themselves. It is, however, also possible to provide separate transmission/reception means for the transmission of the patient-specific signals on the one hand and the MAC addresses for the identification of the peripheral device on the other hand. For example, transmission/reception means for inductive data transmission can also be used for the identification, said means being part of an inductive battery charging device provided in the charging shell.

After identification of the peripheral device, the operative must allocate the identified peripheral device 5 to the patient, who is connected to treatment unit 1 which has identified the peripheral device. For this purpose, the operative must take the peripheral device out of the accommodation unit.

Constant monitoring is carried out to check whether the peripheral device is still located in the accommodation unit. When the operative takes the peripheral device out of the accommodation unit, this is immediately detected by means 16, which generates a status signal indicating that the operative has removed the peripheral device from the accommodation unit. This status signal is sent to the treatment unit, which receives the status signal. With the reception of the status signal for the removal of the peripheral device from the accommodation unit, the treatment unit starts up means (timer) 18 for measuring the time that has passed after the removal of the peripheral device.

The operative must now connect the peripheral device to the patient within a preset time interval. The remaining time in the preset time interval is displayed to the operative on a display unit 13 of treatment unit 1.

When the operative has fitted the peripheral device to the patient and has activated the peripheral device, sensors 6 of the peripheral device receive the physiological measured values, such as the patient's blood pressure and pulse. The signals received from sensors 6 are evaluated by means 20 for checking the allocation of a peripheral device to a patient. This event is signaled by means 20 of peripheral device 5 to treatment unit 1 by the fact that the peripheral device sends to the treatment unit a status signal for the successful allocation of the peripheral device to the patient.

The treatment unit continuously checks whether the status signal for the successful allocation of the peripheral device and patient is received during the preset time interval. If the preset time interval has lapsed before reception of the status signal for the successful allocation of the peripheral device and patient, the treatment unit emits with alarm emitter 12 an optical and/or acoustic alarm signal, with which the operative is prompted to place the peripheral device back into the accommodation unit. At the same time, or alternatively, a corresponding display can also take place on display unit 13. The routine described above then begins afresh.

If, however, the status signal for the successful allocation of the peripheral device and patient is received, there appears on display unit 13 (display) of the treatment unit an indication which prompts the operative to press an acknowledge button 19. The treatment unit waits until button 19 is pressed.

The operative must now check whether patient 2, to whom peripheral device 5 is connected, is the patient to whom treatment unit 1 is connected to which the peripheral device has been allocated by accommodation unit 14. If this is the case, the operative presses acknowledge button 19, which is provided on the peripheral device. A signal for the acknowledgement by the operative is then sent to the treatment unit, which receives the status signal.

It is, however, also possible for the acknowledge button to be located on the treatment unit. It is then not necessary to send the status signal for the acknowledgement of the allocation of the peripheral device and patient to the treatment unit.

Treatment unit 1 now checks whether the operative has acknowledged the correct allocation of the peripheral device and patient by pressing button 19 within the preset time interval.

Treatment unit 1 has means 17, with which the peripheral device is released. Only in the case where acknowledge button 19 has been pressed within the preset time interval do means 17 release the peripheral device, so that the patient-specific data are transmitted from the peripheral device to the treatment unit with radio transmitter/receiver 7, 10. Means 17 must also release the treatment. The treatment program can now be started.

The means described above can form separate modules, but in practice the means are a component of a microprocessor, which is generally provided anyway in the treatment units and peripheral devices.

In the embodiment described by reference to the figures, individual means are allocated in each case to the blood treatment units and individual means are allocated in each case to the peripheral devices. The means which are allocated to the blood treatment units, however, may also be allocated to the peripheral devices. For example, the means for the acknowledgement of the allocation of the patient and treatment unit may be provided not on the peripheral device, but on the treatment unit. The means for emitting an acoustic and/or optical alarm can also be provided on the peripheral device instead of on the treatment unit.

Even though the figures show an arrangement of peripheral devices and treatment units, it can be seen from the description that the peripheral devices and the treatment units are independent devices which have the described modules.

The invention claimed is:

1. An arrangement comprising:
   at least two medical treatment units; and
   at least two peripheral devices,
   wherein a first medical treatment unit of the at least two medical treatment units and a first peripheral device of the at least two peripheral devices are configured to be allocated to a patient, and the first peripheral device comprises a first connector, the first peripheral device and the first treatment unit together including
   a system of at least one of tubes or lines configured for connecting the patient to the first treatment unit to thereby allocate the first medical treatment unit to the patient,
   an accommodation unit fixed to the first medical treatment unit, configured to receive the first peripheral device, and comprising a second connector configured to connect with the first connector,
   a data transmission system comprising a transmitter in the first peripheral device and a receiver in the first medical treatment unit, and being configured such that, when the first peripheral device is received in the accommodation unit the transmitter sends address information to the receiver and the first medical treatment unit identifies the first peripheral device as being allocated to the first medical treatment unit,
   a detector for detecting when the first peripheral device is removed from the accommodation unit,
   a physiological sensor for detecting patient-specific data of the patient, wherein the first peripheral device comprises the physiological sensor and the data transmission system is configured to transmit a status signal to both the first peripheral device and the first medical treatment unit, indicating that the first peripheral device has been allocated to the patient,
   an acknowledgement switch or button configured to, upon activation, acknowledge that the first peripheral device and the first medical treatment unit have been allocated to the same patient,
   a display comprising a prompt that prompts an operator to activate the acknowledgement switch or button once the receiver receives the status signal, and
   a processor configured to release the peripheral device such that the transmitter sends the patient-specific data to the receiver only on condition that the correct allocation of the peripheral device to the patient has been acknowledged.

2. The arrangement according to claim 1, wherein the data transmission system comprises a radio transmitter/receiver in the first peripheral device and a radio transmitter/receiver in the first medical treatment unit.

3. The arrangement according to claim 1, wherein the detector is configured to detect when the first peripheral device is accommodated in the accommodation unit.

4. The arrangement according to claim 3, wherein the first peripheral device is received in and contacts the accommodation unit through mechanical contact makers.

5. The arrangement according to claim 3, wherein the accommodation unit includes a charging unit, the first peripheral device comprises a power supply including a battery, and the charging unit is configured to charge the battery of the power supply of the first peripheral device.

6. The arrangement according to claim 3, wherein the accommodation unit and the detector are configured to cooperate with the first peripheral device in such a way that, after detection of the first peripheral device, the first peripheral device sends a media access control address, for identification, to the first medical treatment unit and the first medical treatment unit receives the media access control address for identification of the first peripheral device.

7. The arrangement according to claim 2, wherein the transmitter/receiver in the first peripheral device is configured to wirelessly transmit signals and the transmitter/receiver in the first medical treatment unit is configured to wirelessly receive signals.

8. The arrangement according to claim 1, wherein the receiver comprises a radio transmitter/receiver and the transmitter comprises a radio transmitter/receiver.

9. The arrangement according to claim 1, wherein the processor is configured to cooperate with a timer configured to measure a time after removal of the first peripheral device from the accommodation unit in such a way that, when patient-specific data are received, it is concluded that there is a successful allocation of the first peripheral device to the patient only when the first peripheral device has been acknowledged by activation of the acknowledgement switch or button within a preset time interval.

10. The arrangement according to claim 9, wherein the display is configured to display a remaining time in the preset time interval within which an acknowledgement by activation of the acknowledgement switch or button, to indicate allocation of the first peripheral device to the patient, has to take place.

11. The arrangement according to claim 1, further comprising an alarm emitter configured to emit an optical and/or acoustic signal, said alarm emitter being designed in such a way that the optical and/or acoustic signal is emitted if, within a preset time interval after removal of the first peripheral device from the accommodation unit, the first peripheral device has not been successfully allocated to the treatment unit.

12. The arrangement according to claim 1, wherein the acknowledgement switch or button comprises a pushbutton or an inductive switch.

13. The arrangement according to claim 1, wherein the first medical treatment unit is a blood treatment apparatus comprising an extracorporeal blood circuit.

14. The arrangement according to claim 1, wherein the first peripheral device includes at least one sensor for measuring a patient's blood pressure, pulse, or both.

15. An alarm system comprising:
a medical treatment unit configured to administer medical treatment to a patient connected to the medical treatment unit via a system of at least one of tubes or lines, the medical treatment unit comprising a radio transmitter/receiver and an accommodation unit, the accommodation unit comprising a power supply and a first electrical connection; and
a peripheral device configured to be connected to the patient and comprising a sensor configured to generate a patient signal corresponding to a physiological aspect of the patient, wherein the sensor comprises at least one of a blood pressure sensor and a pulse sensor, the peripheral device further comprising a second radio transmitter/receiver, a battery, and a second electrical connection and being configured to be received in the accommodation unit such that an electrical connection is made between the first and second electrical connections and the battery is charged by the power supply,
wherein the medical treatment unit and the peripheral device together include
a connection sensor configured to detect a coupling of the peripheral device with the accommodation unit, the connection sensor comprising electrical contacts and configured to generate a status signal when the coupling is detected, the connection sensor being operatively connected to the second radio transmitter/receiver of the peripheral device and configured to prompt the second radio transmitter/receiver of the peripheral device to send an address for the identification of the peripheral device to the radio transmitter/receiver of the medical treatment unit thereby enabling the medical treatment unit to identify the peripheral device,
an acknowledgement switch or button configured to send an acknowledgement signal to the medical treatment unit upon activation of the acknowledgement switch or button,
a processing module configured to check an allocation of the peripheral device to the patient by evaluating the patient signal corresponding to the physiological aspect of the patient, and to (1) generate an alarm signal if, based on the evaluation of the patient signal, the peripheral device is determined not to be allocated to the patient, or (2) prompt an operator to activate the acknowledgment switch or button if, based on the evaluation of the patient signal, the peripheral device is determined to be allocated to the patient,
a processing module configured to transmit patient-specific data, sensed by the sensor, via the second radio transmitter/receiver, from the peripheral device to the radio transmitter/receiver of the medical treatment unit for use in a treatment program only on condition that the correct allocation of the peripheral device to the patient has been acknowledged by activation of the acknowledgment switch or button within a preset time interval, and
an alarm emitter configured to emit an optical and/or acoustic alarm when an alarm signal generated by the processing module configured to check, is received.

16. The alarm system according to claim 15, wherein the processing modules are components of a microprocessor.

17. A method, comprising:
connecting a treatment unit to a patient via a system of at least one of tubes or lines for connection of the patient to the treatment unit, the treatment unit comprising a radio transmitter/receiver and an accommodation unit, the accommodation unit comprising a power supply and a first electrical connection, allocating a peripheral device to the treatment unit and the patient, the peripheral device configured being connected to the patient and comprising a sensor configured to generate a patient signal corresponding to a physiological aspect of the patient, wherein the sensor comprises at least one of a blood pressure sensor and a pulse sensor, the peripheral device further comprising a second radio transmitter/receiver, a battery, and a second electrical connection and being configured to be received in the accommodation unit such that an electrical connection is made between the first and second electrical connections and the battery is charged by the power supply, the allocating comprising detecting a coupling of the peripheral device to the accommodation unit with a connection sensor comprising electrical contacts and configured to generate a status signal when the coupling is detected, the connection sensor being operatively connected to the second radio transmitter/receiver of the peripheral device and configured to prompt the second radio transmitter/receiver of the peripheral device to send an address for the identification of the peripheral device to the radio transmitter/receiver of the treatment unit thereby enabling the treatment unit to identify the peripheral device, checking, via the microprocessor, the allocation of the peripheral device to the patient by evaluating a signal corresponding to a physiological aspect of the patient, and either (1) generating an alarm signal if, based on the evaluation of the patient signal, the peripheral device is determined not to be allocated to the patient, or (2) prompting an operator to activate an acknowledgment switch or button if, based on the evaluation of the patient signal, the peripheral device is determined to be allocated to the patient, activating an acknowledgement switch or button configured to send an acknowledgement signal to the treatment unit upon activation of the acknowledgement switch or button, to acknowledge that the peripheral device and the treatment unit have been allocated to the same patient, and transmitting patient-specific data, sensed by the sensor, with the second radio transmitter/receiver, from the peripheral device to the radio transmitter/receiver of the treatment unit, for use in a treatment program only on condition that the correct allocation of the peripheral device and the patient has been acknowledged by activation of the acknowledgement switch or button within a preset time interval.

18. The method according to claim 17, wherein the allocation of the peripheral device to the treatment unit, the checking of the allocation of the peripheral device to the patient, and the releasing of the peripheral device are all performed by processing modules.

* * * * *